United States Patent
Haenggi et al.

(10) Patent No.: US 9,011,390 B2
(45) Date of Patent: Apr. 21, 2015

(54) METHOD AND DEVICE FOR MICRO-DOSING A LIQUID

(71) Applicant: Roche Diagnostics International AG, Rotkreuz (CH)

(72) Inventors: Roger Haenggi, Nunningen (CH); Hanspeter Niklaus, Riken (CH)

(73) Assignee: Roche Diagnostics International AG, Rotkreuz (CH)

( * ) Notice: Subject to any disclaimer, the term of this patent is extended or adjusted under 35 U.S.C. 154(b) by 224 days.

(21) Appl. No.: 13/803,070

(22) Filed: Mar. 14, 2013

(65) Prior Publication Data

US 2013/0221023 A1 Aug. 29, 2013

Related U.S. Application Data

(63) Continuation of application No. 12/818,298, filed on Jun. 18, 2010, now Pat. No. 8,419,691, which is a continuation of application No. PCT/EP2008/010626, filed on Dec. 13, 2008.

(30) Foreign Application Priority Data

Dec. 18, 2007 (EP) .................................... 07024466

(51) Int. Cl.
- *A61M 5/00* (2006.01)
- *B65D 83/00* (2006.01)
- *A61M 5/145* (2006.01)
- *A61M 5/142* (2006.01)

(52) U.S. Cl.
CPC ........ *B65D 83/0005* (2013.01); *A61M 5/14244* (2013.01); *A61M 5/1452* (2013.01)

(58) Field of Classification Search
USPC ................................... 604/207, 211
See application file for complete search history.

(56) References Cited

U.S. PATENT DOCUMENTS

| | | | |
|---|---|---|---|
| 4,634,431 | A | 1/1987 | Whitney et al. |
| 5,690,618 | A | 11/1997 | Smith et al. |
| 6,248,093 | B1 | 6/2001 | Moberg |
| 2001/0034506 | A1 | 10/2001 | Hirschman et al. |
| 2008/0033369 | A1 | 2/2008 | Kohlbrenner et al. |

FOREIGN PATENT DOCUMENTS

| | | |
|---|---|---|
| WO | 01/83005 A1 | 11/2001 |
| WO | 02/30554 A2 | 4/2002 |
| WO | 03/099357 A1 | 12/2003 |

OTHER PUBLICATIONS

International Search Report, Appln. No. PCT/EP2008/010626, fileld Dec. 13, 2008. Search report completion date is Apr. 16, 2009, pp. 1-8.

*Primary Examiner* — Kevin C Sirmons
*Assistant Examiner* — Deanna K Hall
(74) *Attorney, Agent, or Firm* — Dinsmore & Shohl LLP (57) ABSTRACT

Methods and devices for micro-dosing a liquid are disclosed herein. According to one embodiment, a method for a time controlled micro-dosing of a liquid from a liquid reservoir includes: receiving the liquid reservoir with a structure wherein the structure is portable; securing the liquid reservoir to the structure; connecting a second end of a drive unit to a piston disposed within the liquid reservoir; activating a drive motor; displacing the drive unit with respect to the structure towards the piston in an axial direction with the drive motor; moving the piston axially within the liquid reservoir; and micro-dosing the liquid from the liquid reservoir.

20 Claims, 2 Drawing Sheets

Fig. 2

METHOD AND DEVICE FOR MICRO-DOSING A LIQUID

CROSS REFERENCE TO RELATED APPLICATIONS

This application is a continuation of U.S. patent application Ser. No. 12/818,298 filed Jun. 18, 2010 which is a continuation of International Application No. PCT/EP2008/010626 filed Dec. 13, 2008 which claims priority to European Patent Application No. EP07024466.0 filed on Dec. 18, 2007.

TECHNICAL FIELD

The embodiments described herein relate to methods and portable devices for micro-dosing a liquid and for dispensing a liquid drug.

BACKGROUND

In the pharmaceutical and chemical industries, liquid substances are commonly micro-dosed, i.e. dosed in the range of micro-liters. For example, in some medical applications liquid drugs are administered to a patient's body via micro-dosing.

Patients frequently utilize portable computer controlled micro-dosing devices to administer medication for the treatment of diabetes and in certain pain treatments. The micro-dosing devices can continuously administer medication to a patient as needed throughout the day depending on the demands of the patient. Additionally, the micro-dosing devices may include a drug reservoir which contains a several days supply of medication. Such micro-dosing devices may also be capable of administering the medication subcutaneously. For example, many insulin pumps contain a supply of medication that is administered to the patient's body according to a predetermined daily profile via an infusion cannula.

Since the continuous administration of medication takes place during daily activities, it is desirable to conceal the micro-dosing devices while they are being carried by the patient. Additionally, it is desirable for the micro-dosing devices to be small in order to be concealed by clothing when worn at the patient's body and for wearing comfort.

The outer dimensions of many portable micro-dosing devices are commonly influenced by the space requirements of the liquid reservoir and of a drive unit of the device. One type of micro-dosing device employs a disposable vial with a displacement piston as a liquid reservoir and a drive unit, respectively. A liquid drug is stored in the disposable vial and dispensed from the disposable vial by moving the displacement piston towards the discharge end of the disposable vial.

U.S. Pat. No. 6,248,093 B1 describes embodiments of micro-dosing devices with drive units and reservoirs in various arrangements. In some embodiments the drive unit comprises a drive motor arranged beside the reservoir. Such micro-dosing devices include a transmission gear, which causes additional costs and friction. Furthermore, the transmission gear is prone to wear and tear, and increases the space requirements of the micro-dosing device.

In another embodiment of U.S. Pat. No. 6,248,093 B1, the micro-dosing device comprises a drive motor arranged in line with a liquid reservoir and a threaded appendix of a reservoir piston. The reservoir piston engages a gear wheel of the drive motor with its thread and is thereby linearly displaceable by the drive motor for pushing the piston of the reservoir. The piston is pushed in a retracted position that axially extends substantially over the entire length of the drive motor at the outer periphery thereof, resulting in a relative compact design. However, the threaded appendix at its side facing away from the gear wheel of the drive motor needs to be supported, in which a backlash free arrangement is necessary in order to ensure precise dosing. In such an arrangement, considerable friction and asymmetric transmission of forces into the piston are generated. As a result, imprecision is caused by the tilting of the piston and the deformation of parts under load.

In a further embodiment of U.S. Pat. No. 6,248,093 B1, the micro-dosing device comprises a drive unit having a drive motor with a reduction gear, both arranged in line with a reservoir. A threaded sleeve engages a gear wheel of the drive unit and is thereby linearly displaceable by the drive unit for actuating a piston of the reservoir, in a retracted position that completely circumferentially surrounds the reduction gear but not the drive motor. The length of the motor adds to the length of the micro-dosing device and the outer diameter of the threaded bushing is correlated with the minimum inner diameter of the reservoir. Thus, even though from a mechanical point of view this design avoids the disadvantages of the before mentioned embodiments, it is unsatisfactory as the length and the thickness of the micro-dosing device are increased.

Hence, it is a desire to provide a method of and a portable device for micro-dosing a liquid, which at least partially avoid the disadvantages of the above mentioned prior art.

SUMMARY

According to one embodiment, a method for a time controlled micro-dosing of a liquid from a liquid reservoir includes: receiving the liquid reservoir with a structure wherein the structure is portable; securing the liquid reservoir to the structure; connecting a second end of a drive unit to a piston disposed within the liquid reservoir; activating a drive motor; displacing the drive unit with respect to the structure towards the piston in an axial direction with the drive motor; moving the piston axially within the liquid reservoir; and micro-dosing the liquid from the liquid reservoir.

In another embodiment, a micro-dosing device for micro-dosing a liquid from a liquid reservoir includes a structure. The liquid reservoir is received within the structure and comprises a displacement piston. A drive unit comprises a first end, a second end, and a drive motor. A coupling member is disposed at the second end of the drive unit and removably coupled to the displacement piston. The displacement piston moves axially and dispenses the liquid from the liquid reservoir when the drive motor activates and axially displaces the drive unit relative to the structure.

Further preferred embodiments of the invention become apparent from the dependent claims and from the following description by way of the drawings.

DETAILED DESCRIPTION

One embodiment of the present disclosure provides a method of micro-dosing a liquid from a liquid reservoir comprising a displacement piston arranged within the liquid reservoir such as, for example, a vial-type liquid reservoir. The liquid is micro-dosed by axially moving the displacement piston within the liquid reservoir towards a discharge end to displace the liquid from the liquid reservoir. The liquid is dispensed according to a specific profile over time according to a pre-selected daily profile, which results in a time controlled dispensation of liquid. For example, liquid drugs such as, for example, insulin, are micro-dosed to a patient's body. It is noted that the term "micro-dose," as used herein, means a controlled dispensing of liquid substances in the range of micro-liters, as is typically applied in the pharmaceutical and chemical industry.

In another embodiment, a portable structure for receiving the liquid reservoir is provided.

In a further embodiment, a drive unit for generating the forces for axially moving the displacement piston of the liquid reservoir is provided. The drive unit comprises a first end, a second end and a drive motor. By activating the drive motor, the drive unit is axially displaced relative to the structure.

In yet a further embodiment, the second end of the drive unit is coupled to the displacement piston of the liquid reservoir. While, the liquid reservoir is secured to the structure and immobilized relative to the structure in displacement direction of the displacement piston.

In a further embodiment, the drive motor is activated and moves the drive unit axially moved towards the displacement piston of the liquid reservoir. The displacement piston moves axially within the liquid reservoir towards the discharge end and causes liquid to be dispensed out of the reservoir.

The micro-dosing of liquid from a liquid reservoir, such as, for example, a vial-type reservoir, provides for a compact arrangement that is precise and reliable. Therefore, embodiments of the present disclosure relate to compact and portable micro-dosing devices for liquid medicaments such as, for example, insulin.

In an embodiment of the present disclosure, the drive unit is axially displaced by rotating a rotatable member coupled to the drive unit and having an outer thread. The outer thread engages an inner thread of a sleeve, which is integrally formed by or secured to the structure of the device and immobilized. The sleeve is immobilized in the axial direction along the axis of rotation of the rotatable member facing away from the liquid reservoir. Additionally, the sleeve is rotationally immobile to rotation relative to the structure about the axis of rotation. Such embodiments provide for a sturdy mechanism for effecting the axial movement of the drive unit. Furthermore, sensitive displacement control is provided, e.g. by way of a control unit with an encoder coupled to the drive shaft of the drive motor.

In another embodiment the sleeve comprises an inner thread that engages an outer thread of the rotatable member. The drive unit dispenses liquid from the liquid reservoir as the drive unit is axially displaced from a retracted position to an extended position. The drive unit is in the retracted position when the second end of the drive unit is at its closest position to the inner thread of the sleeve. For example, the drive unit is in the retracted position when a new or completely filled liquid reservoir is received in the structure and is coupled to the second end of the drive unit. The drive unit is in the extended position when the second end of the drive unit at its furthermost location from the inner thread of sleeve. For example, the drive unit is in the extended position when the displacement piston has been pushed to the discharge end of the liquid reservoir, and the liquid the reservoir has been emptied. When the drive unit is in the retracted position, the first end of the drive unit is at least partially circumferentially surrounded by the inner thread of the sleeve. In one embodiment, portions of the inner thread of the sleeve are facing towards the drive unit, and the portions span at least 180° (360° is the complete circumference) of the circumference of the drive unit. For example, where two areas of the inner thread of the sleeve each circumferentially extend over 5° of the circumference of the first end of the drive unit, and are positioned opposite to each other (180°) with the first end of the drive unit arranged between them. In another example, where three areas of the inner thread are equally distributed over the circumference of the first end of the drive unit. In a further example, where the inner thread consists of one area only, which covers an angle of more than 180° of circumference of the first end of the drive unit. Thusly, the drive unit with its rotatable member and the sleeve form a telescopic drive mechanism for transmitting a sturdy and reliable force.

In yet a further embodiment, the activity of the drive unit is monitored by an encoder arranged at the drive unit and associated with a computerized control unit. This association establishes a closed loop control of the displacement position of the drive unit relative to the structure and therefore of the amount of liquid dispensed. In one embodiment, where the drive motor is a rotating motor, the encoder monitors the total or relative number of revolutions or a total or relative angle of rotation of the drive shaft of the drive motor. In other embodiments, where the drive motor is a linear motor, the encoder monitors the absolute or relative linear displacement of the actuator the motor or drive unit directly.

In yet a further embodiment, the forces exerted on the displacement piston of the liquid reservoir are monitored with a force sensor and are associated with the computerized control unit in order to detect an operational disorder such as, an occlusion in the liquid path downstream of the reservoir, a tilted piston, an empty liquid reservoir, and the like.

In yet a further embodiment comprising a sleeve, the power for operating the drive motor is supplied via one or several anti-rotation elements. The anti-rotation elements are arranged between the drive unit and the sleeve in order to prevent rotation of the drive unit relative to the sleeve and to the structure. For example, the power may be supplied by wires, flexprints, or sliding contacts. Thusly, energy is supplied simply and reliably to the drive unit.

In yet a further embodiment, the drive motor is activated by the computerized electronic control according to a specific activity profile. This results in the time-controlled dispensing of liquid from the liquid reservoir. In one embodiment a liquid medicament such as, for example, insulin may be dispensed for the treatment of a disease such as, for example, diabetes. For example, the treatment is conducted according to a daily dispensing profile which may however differ from day to day, or differ on weekends compared to weekdays. In further embodiments, encoders and/or force sensors are employed, and connected to the computerized control unit in order to establish a closed loop control and/or respective alarm functions.

In another embodiment of the present disclosure a micro-dosing device is a portable device. The micro-dosing device micro-doses of a liquid from a liquid reservoir that is releasably received inside the device. The liquid is micro-dosed by axially moving a displacement piston arranged within the liquid reservoir to displace liquid from the liquid reservoir. In one example, the liquid reservoir is a vial containing a liquid medicament such as, for example, insulin.

According to one embodiment the micro-dosing device comprises a structure for receiving the liquid reservoir and a drive unit for generating the forces for axially moving a displacement piston. The drive unit comprises a drive motor, a first end and a second end. The drive unit axially displaces relative to the structure when the drive motor is activated. The second end of the drive unit comprises a coupling member that releasably couples the drive unit to the displacement piston of the liquid reservoir. The displacement piston moves axially within the liquid reservoir towards a discharge end of the liquid reservoir upon an axial movement of the drive unit. This axial motion of the displacement piston dispenses liquid from the opening in the discharge end. Additionally, it is noted that, since the coupling member is coupled in a releasable manner, the micro-dosing device is suitable for multiple use.

In another embodiment, the micro-dosing device is an ultra compact portable device for micro-dosing liquid medicaments from a vial-type reservoir.

In yet another embodiment, the micro-dosing device comprises a rotatable member and a sleeve. The rotatable member rotates about an axis of rotation and comprises an external thread coaxially arranged about the axis of rotation. The sleeve is integrally formed by or is secured to the structure of the micro-dosing device. The sleeve comprises an inner thread that engages the outer thread of the rotatable member. The rotatable member is coupled to the drive unit at the first end of the drive unit, and upon activation of the drive motor of the drive unit, the rotatable member is rotated around the axis of rotation. Thusly, the rotatable member and the drive unit move axially relative to the sleeve and to the structure of the micro-dosing device. Such a micro-dosing device has a sturdy mechanism for the axial displacement of the drive unit. Additionally, the micro-dosing device may comprise an encoder coupled to the drive shaft of the drive motor having an associated control for precise displacement control.

In a further embodiment of the micro-dosing device the sleeve comprises an inner thread. The micro-dosing device further comprises a rotatable member and a drive unit having a drive motor. The drive motor activates and causes a subsequent rotation of the rotatable member. The drive unit is axially displaced relative to the sleeve and the structure, and moves from a retracted position to an extended position. In one embodiment the drive unit is in the retracted position when the second end of the drive unit, which is coupled to the displacement piston of the liquid reservoir, is its closest position to the inner thread of the sleeve. For example, when a new, completely filled liquid reservoir is installed within the micro-dosing device. In one embodiment, the drive unit is in the extended position when the second end of the drive unit is in its furthest position away from the inner thread of the sleeve. For example, when an empty liquid reservoir is installed within the micro-dosing device. When the drive unit is in the retracted position the inner thread of the sleeve at least partially circumferentially surrounds at least the first end of the drive unit. Additionally, it is noted that, the drive unit may be in further positions between the retracted and the extended position while having positions distributed about the circumference of the first end faced by the inner thread of the sleeve over an angle greater than 180° portions. For example, two areas of the inner thread of the sleeve each cover a small angle of circumference of the first end are positioned opposite to each other with the first end of the drive unit arranged between them. In another example, e.g. three areas of the inner thread are equally distributed over the circumference of the first end. In yet another example, the inner thread comprises one area which covers an angle of more than 180° of circumference of the first end of the drive unit. Thusly, the drive unit having a rotatable member together with the sleeve forms a telescopic drive mechanism for sturdy and reliable force transmission.

In yet a further embodiment of the micro-dosing the inner thread of the sleeve at least partly circumferentially surrounds, in the fashion described hereinabove, not only the first end of the drive unit but at least half of the length of the drive unit when the drive unit is in a retracted position. In another embodiment the inner thread of the sleeve circumferentially surrounds the entire length of the drive unit. Thusly, the drive unit with its driven rotatable member together with the sleeve forms a telescopic drive mechanism having a good ratio between retracted and extended length.

In a further embodiment of the micro-dosing device comprises a sleeve comprising an inner thread disposed at the interior of the sleeve. The second end of the drive unit protrudes out of one end of the sleeve in both the retracted position and the extended position. Additionally, the drive unit having a rotatable member received within the sleeve forms a compact, enclosed telescopic drive mechanism which can be provided as a module.

In another embodiment a sealing member is disposed between the end of the sleeve and the drive unit, such as, for example an O-ring. The sealing member prevents dirt or liquid from entering into the sleeve.

In a further embodiment of the micro-dosing device, the drive unit further comprises a reduction gear arranged between the drive motor and the rotatable member. For example, a relatively small motor can be employed that provides a suitable amount of torque for rotating the rotatable member and a sensitive displacement control. Furthermore, the reduction gear is disposed at the first end of the drive unit, and disposed between the drive motor and the rotatable member. Thus, the drive unit can be designed to be slim.

In yet a further embodiment of the micro-dosing device, the drive motor comprises a drive shaft defining a driving axis of rotation. In another embodiment, the driving axis of rotation and the axis of rotation of the rotatable member are coaxially aligned, promoting a slim and compact design.

In yet a further embodiment of the micro-dosing device, the drive unit comprises an encoder associated with a computerized control unit that monitors the activity of the drive unit and establishes a closed loop control of the displacement position of the drive unit relative to the structure. Such a displacement control also controls the amount of liquid dispensed. In other embodiments, the drive motor is a rotating motor, and the encoder monitors the total or relative number of revolutions or a total or relative angle of rotation of the shaft of the motor. In further embodiments a linear motor is employed, and the encoder monitors the absolute or relative linear displacement directly.

In another embodiment the encoder is arranged at the second end of the drive unit. In other embodiments, the encoder is at least partially disposed inside a protrusion. For example, the protrusion is formed where the displacement piston of the liquid reservoir is coupled to the second end of the drive unit, and at least partially received inside the displacement piston. Therefore, the encoder can be used without increasing the length of the micro-dosing device.

In yet a further embodiment of the micro-dosing device, an anti-rotation element is disposed between the drive unit and the sleeve to prevent a rotation of the drive unit relative to the sleeve. However, the anti-rotation element permits axial movement of the drive unit relative to the sleeve. In other embodiments the micro-dosing device comprises a sleeve encapsulating all of the mechanical parts for effecting the axial displacement of the drive unit, thereby forming a modular element.

In another embodiment, power for operating the drive motor is supplied via the anti-rotation elements by wires, flexprints, sliding contacts established between components of the anti-rotation elements, and the like. Thus, a reliable transmittal of the energy for the drive can be achieved.

In yet a further embodiment, the micro-dosing device comprises a force sensor associated with controls to permit the monitoring of the forces that are exerted upon the displacement piston in operation. Operational disorders such as, for example, an occlusion in the liquid path downstream of the reservoir, a tilted piston, or an empty liquid reservoir can be detected. In other embodiments, the force sensor axially supports the sleeve in order to determine of the forces. In other embodiments, the force sensor is included in the coupling member of the drive unit.

In yet a further embodiment of the micro-dosing device, the axis of rotation of the rotatable member is coaxially aligned with a central axis of the displacement piston of the liquid reservoir. The coaxial alignment provides a fully symmetrical transmission of forces from the rotatable member to the displacement piston. Therefore, the bending or tilting of the involved components is reduced. Similarly, the friction between these parts and adjacent stationary parts when moved relative to each other is reduced.

In yet a further embodiment, the micro-dosing device further comprises a computerized control unit that controls the time-controlled dispensation of liquid by the drive unit. For example, the drive motor is activated according to a specific activity profile by an electronic control system for the time-controlled dispensing of liquid from the liquid reservoir. Thus, liquid medicament such as insulin for the treatment of a disease such as diabetes is dispensed according to a daily dispensing profile. The daily dispensing profile may differ from day to day, or be different over the weekend compared to the normal working days. In other embodiments, encoders and/or force sensors are employed, and functionally connected to the computerized control unit in order to establish a closed loop control and/or respective alarm functions.

In yet a further embodiment, the micro-dosing device further comprises a liquid reservoir with a displacement piston received in its structure and coupled to the second end of the drive unit. The liquid reservoir may contain a liquid drug such as, for example, insulin or a liquid pain killer.

Figure 1A:
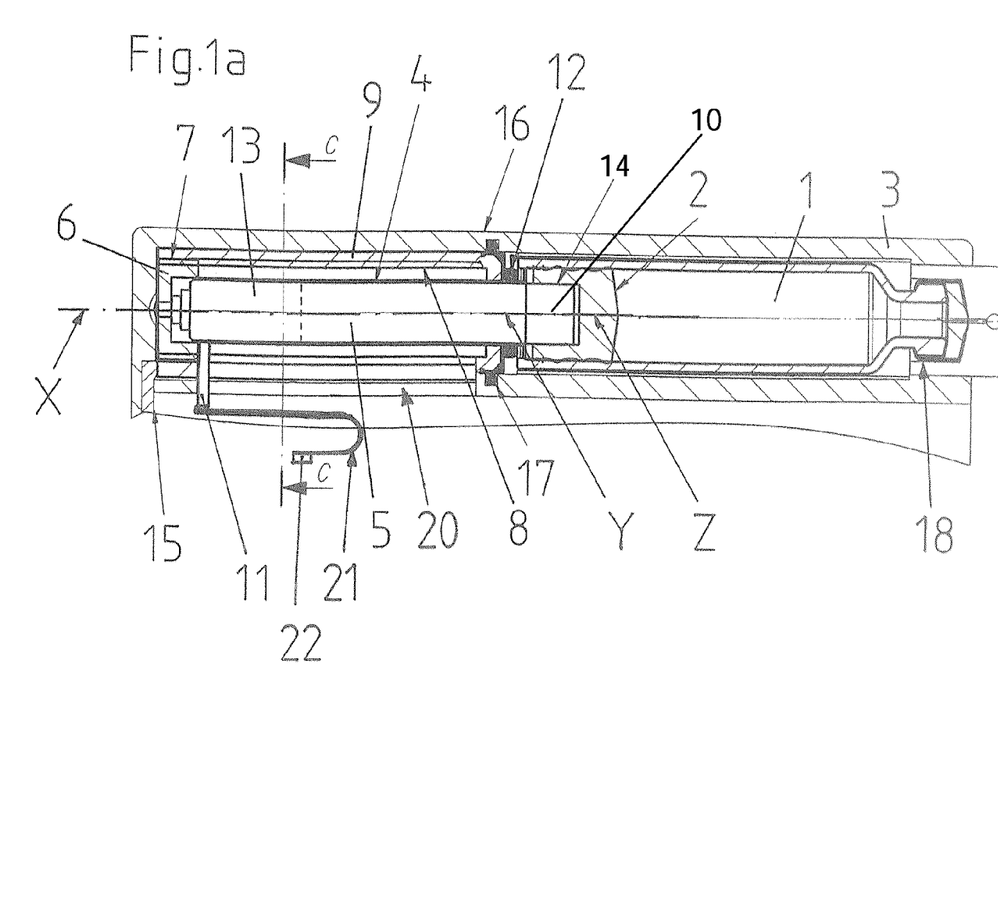
FIG. 1a depicts a sectional view through a portion of a micro-dosing device according to one or more of the embodiments shown and described herein.
Figure 1B:
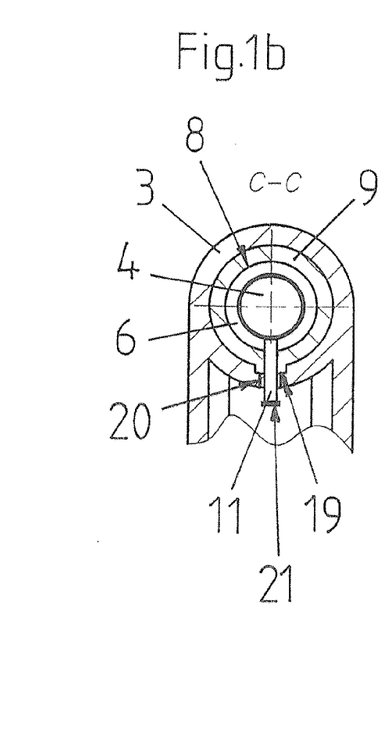
FIG. 1b depicts a cut along line C-C in FIG. 1a according to one or more of the embodiments shown and described herein.
Figure 2:
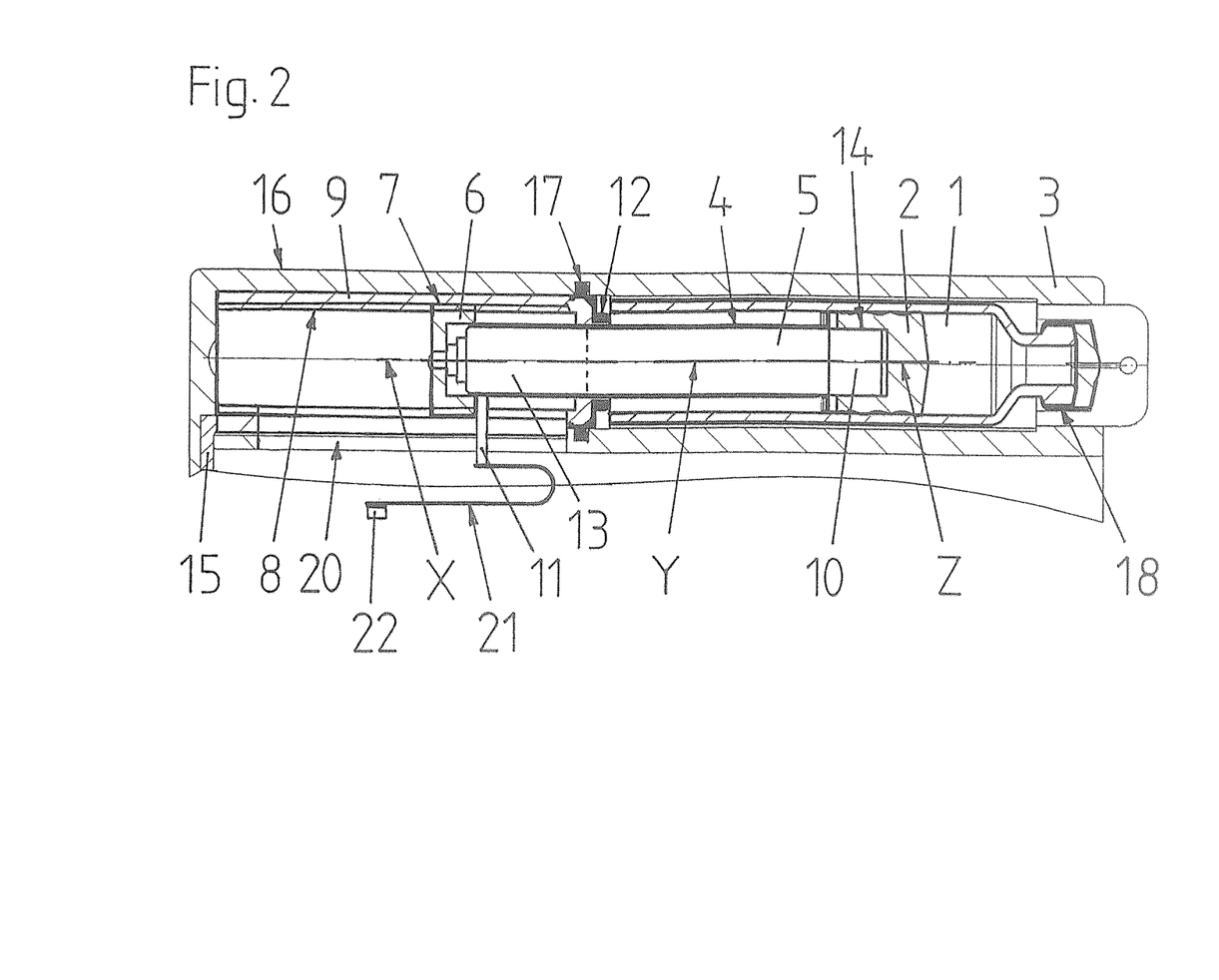
FIG. 2 depicts a sectional view through a portion of a micro-dosing device according to one or more of the embodiments shown and described herein.

In yet a further embodiment, the micro-dosing device dispenses a liquid drug such as, for example, insulin or a liquid pain killer. Referring now to FIGS. 1a-2, a mechanical portion (pump section) of a micro-dosing device according to embodiments of the invention in the form of a portable infusion pump for the time controlled administration of insulin is illustrated, one embodiment in longitudinal section with the pump being equipped with a new, completely filled vial 1 of insulin (FIG. 1a), another embodiment in longitudinal section with the pump being equipped with a used, only partially filled vial 1 of insulin (FIG. 2), and still other embodiment in section along line C-C in FIG. 1a (FIG. 1b). As can be seen from these drawings, the infusion pump comprises a structure 3 which forms a housing 16 of the pump in which a drive unit 4 and a liquid reservoir (i.e., vial) 1 containing insulin are arranged in line. The liquid reservoir 1 comprises a displacement piston 2 having a central axis Z. The displacement piston 2 moves axially within the liquid reservoir 1 towards a discharge end 18 of the liquid reservoir 1 to displace a liquid out of the liquid reservoir 1. The drive unit 4 comprises a drive motor 5, which may be a rotational electric motor, comprising a drive shaft (not shown), a driving axis of rotation Y and a reduction gear 13. The reduction gear 13 comprises a power intake side that is coupled to the drive shaft of the drive motor 5 and a power output side that is coupled to a rotatable member 6. The rotatable member 6 rotates about an axis of rotation X and comprises an outer thread 7 arranged about the axis of rotation X. The rotatable member 6, the reduction gear 13 and the drive motor 5 are arranged in line such that the axis of rotation X of the rotatable member 6 and the driving axis of rotation Y of the drive motor 5 are coaxially aligned. Thus, the reduction gear 13 is disposed between the rotatable member 6 and the drive motor 5. As a result, a first end of the drive unit 4, which comprises the reduction gear 13, faces away from the liquid reservoir 1. A second end of the drive unit 4 comprises a coupling member 14 that protrudes into the displacement piston 2 and releasably couples the drive unit and the displacement piston 2. The drive unit 4 also comprises an encoder 10 disposed within the coupling member 14.

In another embodiment, the outer thread 7 of the rotatable member (e.g., gear wheel) 6 engages an inner thread 8 of a threaded sleeve 9 surrounding same. The sleeve 9 is secured to the structure 3 of the infusion pump in such a manner that, in an axial direction facing away from the liquid reservoir (i.e., vial) 1 and rotationally around the axis X of the gear wheel 6, the sleeve 9 is immobile with respect to the structure 3. For accomplishing this, the sleeve 9 in the axial direction abuts onto a force sensor 15 arranged at the bottom of a cavity provided in the structure 3 for receiving the sleeve 9 (see FIGS. 1a and 2), while rotationally it comprises at its outer periphery a radially protruding rim 19 which engages a corresponding groove in the structure 3 (see FIG. 1b). The drive unit 4 comprises an anti-rotation element 11 that extends radially outward from the periphery of the drive unit 4 through a longitudinal slot 20 formed through the sleeve 9 and through the structure 3. The anti-rotation element 11 together with the longitudinal slot 20 form an anti-rotating element, which prevents a rotation of the drive unit 4 relative to the sleeve 9 but permits axial travel of the drive unit 4 relative to the sleeve 9.

Referring now to FIGS. 1a and 2, according to one embodiment, the drive motor 5 activates and rotates the rotatable member 6 by rotating the reduction gear 13 about the axis of rotation X. The rotatable member 6 travels in an axial direction as the outer thread 7 travels along the inner thread 8 of the sleeve 9. Thusly, the rotatable member 6 displaces the drive unit 4 and the displacement piston 2 relative to the sleeve 9 and the structure 3. The liquid reservoir 1 remains stationary, and the displacement piston 2 travels within the liquid reservoir 1 towards the discharge end 18 of the liquid reservoir 1. As a result, a liquid is dispensed from the liquid reservoir 1. For example, a liquid reservoir 1 filled with insulin dispenses approximately two thirds of the rated volume of insulin within the liquid reservoir 1 as the displacement piston 2 travels from a retracted position (FIG. 1a) to two thirds of its travel way (FIG. 2).

Referring now to FIG. 1b, another embodiment of the drive unit 4 comprises a first end that carries the rotatable member 6. The first end, excepting the longitudinal slot 20 that receives the anti-rotation element 11, is completely enclosed by the inner thread 8 of the sleeve 9, i.e. the inner thread 8 circumferentially surrounds the first end of the drive unit 4 by nearly 360°.

Referring again to FIGS. 1a and 2, in embodiments of the present disclosure the first end of the drive unit 4 remains within the inner thread 8 of the sleeve throughout the displacement range of the drive unit 4. When the drive unit 4 is in the retracted position (FIG. 1a), i.e. in a fully retracted state within the displacement range, the sleeve 9 surrounds the majority of the drive unit 4 with its inner thread 8, and the second end of the drive unit 4 protrudes axially from the sleeve 9.

Further embodiments comprise sealing members 12 and 17 in order to prevent dirt and liquid from entering the sleeve 9 and the area between the sleeve 9 and the structure 3. For example, O-rings are provided as a sealing member 12 between the sleeve 9 and the structure 3 and a sealing member 17 between the sleeve 9 and the second end of the drive unit In additional embodiments, the micro-dosing device comprises a computerized control unit (not shown) comprising a display, a user interface, a power supply and a control board. The computerized control unit receives information from the encoder 10 and the force sensor 15. The computerized control unit controls the drive unit 4. For example, the computerized control unit controls the drive unit 4 to precisely dispense insulin from the liquid reservoir 1 according to a predefined daily profile.

Further embodiments of the micro-dosing device comprise electrical connections between the stationary and the movable electrical parts are established via a flexprint 21, which compensates the relative movement between these parts during operation. In one embodiment the flexprint 21 connects the computerized control unit with the drive motor 5 and the encoder 10. The flexprint 21 provides several electrical lines and mechanically connects one of its ends to the free end of the anti-rotation element 11. The electrical lines electrically connect with corresponding electrical lines arranged within the anti-rotation element 11. The corresponding electrical lines lead to the drive motor 5 and to the encoder 10. The other end of the flexprint 21 connects mechanically and electrically via a connector 22 to the computerized control unit (not shown).

In another embodiment a brushless DC-motor is employed, and the flexprint 21 contains eight electrical lines. Three of the eight electrical lines are connected to the encoder 10, which comprises hall sensors, to control the angular position of the motor shaft. Another three lines are connected to three motor windings completing a three-phased motor arrangement. One of the eight electrical lines is a power line, which in one embodiment is set to 3 volts, and the last line is a connection to ground.

Further embodiments of the micro-dosing device comprise a flexprint 21 arranged directly at the drive unit 4 adjacent the anti-rotation element 11. The flexprint 21 extends through the longitudinal slot 20, which passes through the sleeve 9 and the structure 3, towards the computerized control unit. In still further embodiments, the flexprint 21 is arranged between the drive unit 4 and the sleeve 9. In such an arrangement the moveable parts such as, for example, the drive unit 4, the drive motor 5, the rotatable member 6, and the reduction gear 13, and the flexprint 21 are disposed inside the sleeve 9, and form an enclosed telescopic drive mechanism which can be provided as a module.

What is claimed is:

1. A micro-dosing device for micro-dosing a liquid from a liquid reservoir, the micro-dosing device comprising:
   a structure configured to receive a liquid reservoir;
   a drive unit comprising a first end, a second end, and a drive motor;
   a displacement piston configured to move axially and dispense the liquid from the liquid reservoir when the drive motor activates and axially displaces the drive unit relative to the structure and relative to a sleeve wherein the sleeve comprises an inner thread that engages the outer thread of a rotatable member and the rotatable member is coupled to the first end of the drive unit and comprises an outer thread coaxially arranged around an axis of rotation; and
   an anti-rotation element disposed between the drive unit and the sleeve wherein the anti-rotation element prevents a rotation of the drive unit relative to the sleeve and permits an axial displacement of the drive unit relative to the sleeve and wherein the anti-rotation element extends radially outward from the periphery of the drive unit through a longitudinal slot formed through the structure and through the sleeve.

2. The micro-dosing device of claim 1 further comprising a flexprint coupled to the structure and arranged directly at the drive unit adjacent the anti-rotation element.

3. The micro-dosing device of claim 1 further comprising a flexprint coupled to the structure and configured to establish electrical connections between a computerized control unit, the drive motor, and an encoder.

4. The micro-dosing device of claim 1 wherein portions of the inner thread of the sleeve are facing towards the drive unit, and the portions span at least 180 degrees of a circumference of the drive unit.

5. The micro-dosing device of claim 1 further comprising an encoder coupled to the drive motor and configured to monitor a total or a relative number of revolutions of the drive shaft of the drive motor.

6. The micro-dosing device of claim 1 further comprising an encoder coupled to the drive motor and configured to monitor a relative angle of rotation of the drive shaft of the drive motor.

7. The micro-dosing device of claim 6 wherein the encoder is disposed within a coupling member that is coupled to the drive unit.

8. The micro-dosing device of claim 1 further comprising a force sensor connected to a computerized control unit coupled to the structure to permit the monitoring of forces that are exerted upon the displacement piston in operation such that an empty liquid reservoir can be detected.

9. The micro-dosing device of claim 1 further comprising a force sensor connected to a computerized control unit coupled to the structure to permit the monitoring of forces that are exerted upon the displacement piston in operation such that an occlusion in a liquid path downstream of the liquid reservoir can be detected.

10. The micro-dosing device of claim 1 further comprising a force sensor connected to a computerized control unit coupled to the structure to permit the monitoring of forces that are exerted upon the displacement piston in operation such that a disorder comprising a titled piston can be detected.

11. The micro-dosing device of claim 1 further comprising a computerized control unit coupled to the structure that controls a time-controlled dispensation of liquid by the drive unit and which is functionally connected to an encoder to form a closed loop.

12. The micro-dosing device of claim 1 further comprising a computerized control unit coupled to the structure that controls a time-controlled dispensation of liquid by the drive unit and which is functionally connected to an encoder to establish an alarm function.

13. The micro-dosing device of claim 1 further comprising a computerized control unit coupled to the structure that activates the drive motor according to a specific activity profile provided by an electronic control system for a time-controlled dispensing of liquid from the liquid reservoir.

14. The micro-dosing device of claim 1 further comprising a sealing member coupled to the sleeve and configured so as to prevent dirt and liquid from entering the sleeve and an area between the sleeve and the structure, and wherein the sealing member is an O-ring.

15. The micro-dosing device of claim 1 wherein the sleeve comprises at its outer periphery a radially protruding rim.

16. The micro-dosing device of claim 1 further comprising a reduction gear comprising a power intake side that is coupled to the drive shaft of the drive motor and a power output side that is coupled to the rotatable member.

17. A method for a time controlled micro-dosing of a liquid from a liquid reservoir, the method comprising:
providing a portable structure containing a liquid reservoir secured to the portable structure wherein the structure contains a drive unit connected to a displacement piston disposed within the liquid reservoir, wherein the drive unit has a drive motor, and wherein the drive unit comprises an anti-rotation element that extends radially outward from the periphery of the drive unit through a longitudinal slot formed through the structure and through a sleeve coupled to the structure; and
micro-dosing the liquid from the liquid reservoir by activating the drive motor so as to move the displacement piston axially within the liquid reservoir by rotating with the drive unit a rotatable member coupled to the drive unit, the rotatable member having an outer thread which engages an inner thread disposed on the sleeve, and arranged between the drive unit and the second member is the anti-rotation element preventing rotation of the drive unit relative to the sleeve and permitting axial displacement of the drive unit relative to the sleeve.

18. The method of claim 17 wherein the portable structure further comprises an encoder coupled to the drive motor and wherein a total or a relative number of revolutions of the drive shaft of the drive motor is monitored using the encoder.

19. The method of claim 17 wherein the portable structure further comprises an encoder coupled to the drive motor and wherein a relative angle of rotation of the drive shaft of the drive motor is monitored using an encoder.

20. The method of claim 17 wherein the portable structure further comprises a computerized control unit coupled to the portable structure that controls the time-controlled micro-dosing of the liquid by the drive unit and which is functionally connected to an encoder to establish an alarm function.

* * * * *

UNITED STATES PATENT AND TRADEMARK OFFICE
CERTIFICATE OF CORRECTION

Page 1 of 2

PATENT NO. : 9,011,390 B2
APPLICATION NO. : 13/803070
DATED : April 21, 2015
INVENTOR(S) : Roger Haenggi et al.

It is certified that error appears in the above-identified patent and that said Letters Patent is hereby corrected as shown below:

In the Specification

Col. 1, Line 32,
"devices may include a drug reservoir which contains a several" should read
--devices may include a drug reservoir which contains several--;

Col. 3, Line 27,
"moves the drive unit axially moved towards the displacement" should read
--moves the drive unit axially towards the displacement--;

Col. 3, Line 61,
"extended position when the second end of the drive unit at its" should read
--extended position when the second end of the drive unit is at its--;

Col. 3, Line 65,
"the liquid reservoir, and the liquid the reservoir has been" should read
--the liquid reservoir, and the liquid reservoir has been--;

Col. 4, Line 10,
"where three areas of the inner thread are equally distributed" should read
--three areas of the inner thread are equally distributed--;

Col. 4, Line 12,
"further example, where the inner thread consists of one area" should read
--further example, the inner thread consists of one area--;

Col. 5, Line 43,
"tion to the inner thread of the sleeve. For example, when a" should read
--tion to the inner thread of the sleeve; for example, when a--; and Signed and Sealed this
Fifth Day of April, 2016

Michelle K. Lee
*Director of the United States Patent and Trademark Office*

CERTIFICATE OF CORRECTION (continued)
U.S. Pat. No. 9,011,390 B2

In the Specification

Col. 5, Line 48,
  "sleeve. For example, when an empty liquid reservoir is" should read
  --sleeve; for example, when an empty liquid reservoir is--.